US008676319B2

(12) United States Patent
Knoll

(10) Patent No.: US 8,676,319 B2
(45) Date of Patent: Mar. 18, 2014

(54) IMPLANTABLE MEDICAL DEVICE WITH COMPRESSIBLE FIXATION MEMBER

(75) Inventor: Randall L. Knoll, Stillwater, MN (US)

(73) Assignee: Medtronic, Inc., Minneapolis, MN (US)

(*) Notice: Subject to any disclaimer, the term of this patent is extended or adjusted under 35 U.S.C. 154(b) by 269 days.

(21) Appl. No.: 12/915,935

(22) Filed: Oct. 29, 2010

(65) Prior Publication Data

US 2012/0109272 A1 May 3, 2012

(51) Int. Cl.
*A61N 1/375* (2006.01)

(52) U.S. Cl.
USPC .......................................................... 607/36

(58) Field of Classification Search
USPC ...................................... 607/36–38
See application file for complete search history.

(56) References Cited

U.S. PATENT DOCUMENTS

| 4,943,618 | A | 7/1990 | Stoy |
| 5,252,692 | A | 10/1993 | Lovy |
| 5,645,592 | A | 7/1997 | Nicolais |
| 5,769,882 | A | 6/1998 | Fogarty |
| 7,200,437 | B1 | 4/2007 | Nabutovsky |
| 7,349,742 | B2 | 3/2008 | Heil |
| 7,648,713 | B2 | 1/2010 | Sawhney |
| 7,734,343 | B2 | 6/2010 | Ransbury |
| 2005/0004660 | A1 | 1/2005 | Rosenbluth |
| 2006/0089690 | A1 | 4/2006 | Gerber |
| 2006/0095077 | A1* | 5/2006 | Tronnes ............................ 607/2 |
| 2006/0095078 | A1 | 5/2006 | Tronnes |
| 2006/0241737 | A1* | 10/2006 | Tockman et al. ............ 607/126 |
| 2007/0135916 | A1 | 6/2007 | Maxwell |
| 2008/0103576 | A1 | 5/2008 | Gerber |
| 2009/0182421 | A1 | 7/2009 | Silvestrini |
| 2009/0294049 | A1 | 12/2009 | Udipi |
| 2010/0042195 | A1* | 2/2010 | Cooke et al. .................. 607/120 |
| 2010/0086678 | A1 | 4/2010 | Arthur et al. |

FOREIGN PATENT DOCUMENTS

| EP | 0481042 B1 | 7/1995 |
| EP | 1231950 B1 | 6/2006 |
| WO | 9915211 A1 | 4/1999 |
| WO | 2009089526 A2 | 7/2009 |

OTHER PUBLICATIONS

Yoseph Rozenman, et al. Wireless Acoustic Communication With a Miniature Pressure Sensor in the Pulmonary Artery for Disease Surveillance and Therapy of Patients With Congestive Heart Failure. Journal of the American College of Cardiology, http://content.onlinejacc.org/cgi/content/full/j.jacc.2006.11.021v1, downloaded on Oct. 7, 2010, pp. 784-789.

\* cited by examiner

*Primary Examiner* — Joseph Stoklosa
*Assistant Examiner* — Minh Duc Pham
(74) *Attorney, Agent, or Firm* — Reed A. Duthler; Stephen W. Bauer

(57) ABSTRACT

An implantable medical device and method of implanting a medical device, the device including a housing surrounding an operative component and a resiliently deformable fixation member. The fixation member includes a ring shaped annulus circumscribing the housing and a plurality of elongated struts having a proximal end affixed to the housing and a distal end affixed to the annulus. The fixation member may be comprised of a hydrogel such that it may be in a smaller, dehydrated form during implantation, and then may absorb fluid to expand to a larger, hydrated form after insertion to engage the surrounding tissue.

3 Claims, 4 Drawing Sheets

IMPLANTABLE MEDICAL DEVICE WITH COMPRESSIBLE FIXATION MEMBER

FIELD

The invention relates to implantable medical devices implantable in a human or animal body lumen and, more particularly, fixation structures for securing implantable medical devices.

BACKGROUND

Many implantable medical devices include components that are deployed in particular areas within a human or animal body. In one example, an electrical sensor deployed proximate to a muscle senses activation of the muscle or within an organ or vessel senses physiological parameters. In another example, a neurostimulator deployed proximate to targeted tissue includes electrodes that deliver electrical stimulation therapy to the tissue.

The continuous monitoring of the physical status of patients having chronic illness is essential for ensuring optimal therapy and may be performed by such implantable medical devices. For example, patients having heart diseases benefit from monitoring of their cardiac and circulatory status to adjust their therapy, which may include medication drug therapy or pacing stimulation therapy, to predict acute worsening, and to prevent decompensation. While various methods may be used for monitoring cardiovascular status, implantable measuring devices are preferred over other methods in many cases. Such implantable measuring devices can determine the relevant variables directly in the body and therefore may operate more precisely and reliably than external methods. For example, the blood pressure may be directly measured by such devices within the cardiovascular system and represents an important variable for monitoring cardiovascular status.

With these and other implantable devices, it can be desirable that one or more components remain substantially anchored, so that the components will be less likely to migrate from the desired site of sensing or therapy. Devices that restrict migration of an implanted medical device or a component thereof are called "fixation structures." Fixation structures can anchor a medical device to an anatomical feature, such as an organ or a bone. Fixation structures do not necessarily restrict all motion of the implanted device or its component, but generally reduce the motion of the device or component so that it remains proximate to a desired location. There have been many approaches that address fixation of medical devices. Some devices employ fixed protrusions such as tines to engage body tissue. Other devices use helical securing structures and still others use barbs to hold an implanted medical device in place. Some mechanical fixation structures employ adhesive properties to hold devices in place. When medical devices such as sensors are implanted within vessel walls, they can provide useful information regarding cardiovascular status. However, existing implantable medical devices may become encapsulated as the vessel reacts to the device and tissue grows around the device. Such encapsulation can interfere with the functioning of the device.

SUMMARY

Embodiments of the invention include implantable medical devices, and methods of implanting such devices, the devices including a housing surrounding an operative component such as a sensor or a stimulator, and a resiliently deformable fixation member for supporting the housing. The fixation member includes a ring shaped annulus circumscribing the housing and a plurality of elongated struts having a proximal end affixed to the housing and a distal end affixed to the annulus.

The fixation member may be made from a deformable material such as a hydrogel. For example, the strut and annulus may be integrally formed of a biocompatible hydrogel. The use of a hydrogel allows the device to exist in a compressed, dehydrated form in which the fixation member is smaller and may be implanted more easily, such as through a catheter. In some embodiments, the fixation member may be folded or rolled when in the dehydrated state. After implantation, the hydrogel may absorb fluid, such as fluid present in blood or in interstitial fluid, to expand to a larger, hydrated state to engage the surrounding tissue at the site of implantation. When the device is implanted within a lumen of a vessel, the annulus of the fixation member lies against the wall of the vessel to support the fixation member at a location within the blood flow and away from the vessel wall.

In some embodiments, the struts are curved in shape between the proximal and distal ends. In some embodiments, the struts may be spaced in pairs with each strut curving away from the other of its pair between their proximal and distal ends in a circumferential direction. In other embodiments, the struts are all curved in the same circumferential direction and may be approximately evenly spaced around the circumference of the housing.

In another embodiments, the implantable medical device is designed for implantation into a lumen and includes a housing surrounding an operative component and a resiliently deformable fixation member for supporting the housing. The fixation member includes a thin ring shaped annulus circumscribing the housing, having an outer surface and an inner surface defining a central lumen, and a plurality of elongated struts having a proximal end affixed to the housing and a distal end affixed to the inner surface of the annulus. The fixation member is comprised of an expandable material which allows the fixation member to expand after insertion into a body lumen, and the outer surface of the annulus is sized to abut an inner wall of the vessel lumen when expanded. The expandable material may be a hydrogel and the fixation member may be folded, stretched, rolled, or compressed to reduce the diameter of the medical device.

In another embodiment, a method of implanting an implantable medical device includes inserting a catheter distal end into a patient's body, advancing the catheter to a desired location within a body lumen, and passing the implantable medical device from the catheter and into the patient's body. The implantable medical device includes a housing and a hydrogel fixation member including a plurality of struts and an annulus, with the struts attaching the housing to the annulus, and the annulus circumscribing the housing, and with the hydrogel fixation member in a dehydrated state. The method further includes allowing the hydrogel fixation member to hydrate to expand radially outward to a hydrated state such that an outer surface of the annulus contacts an inner surface of the lumen. The struts may be curved in the circumferential direction between their proximal and distal ends and may be spaced apart to provide openings between the struts through which blood can flow around the implanted device. The fixation member may become hydrated by contacting the device with a body fluid, such as blood or interstitial fluid present at the implantation site. In some embodiments, this method may be used for implanting a medical device which is a sensor into the pulmonary artery.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE PREFERRED EMBODIMENTS

Figure 1:
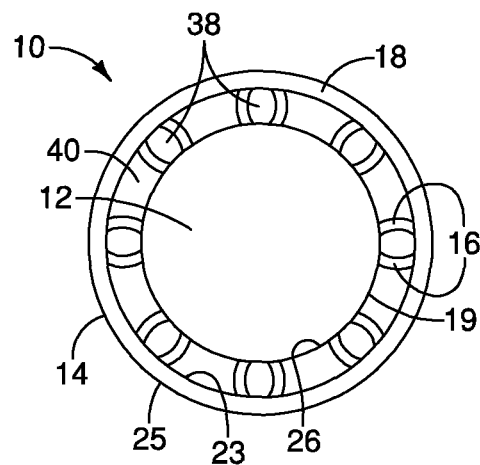
FIG. 1 is a perspective view of an expandable device in an unexpanded state.

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention provide improved implantable medical devices for positioning within a lumen such as a vessel, an organ such as the heart, or a cavity such as the esophagus, stomach, or eye, in a human or animal body. The device includes a non-compressible housing surrounding an operative component and a deformable, compressible fixation member attached to the housing and configured to position the housing away from the wall of the lumen or other surrounding tissue. The fixation member may also be designed to minimize tilt or movement of the sensor which could bring it into proximity with or contact with the lumen wall or other surrounding tissue.

By positioning and maintaining the sensor away from the surrounding tissue such as the vessel wall, embodiments of the invention avoid problems with encapsulation which occurred in prior art devices such as sensors. With prior art devices, when implanted adjacent to a wall of a vessel, there was a risk that the device could become encapsulated over time, resulting in the device being collapsed to the wall of the vessel. Particularly for sensors, this could cause the device to be less effective or even inoperative. Fixation members according to embodiments of the invention therefore position the device away from the surrounding tissue to avoid encapsulation. For example, the fixation member may center the sensor within the lumen, such as with the longitudinal axis of the device extending along or near the central axis of the vessel. In such a location, the device is less likely to become fibrosed by tissue overgrowth which can interfere with functioning. As such, the fixation member allows the device to function better over a longer period of time. Furthermore, if the device is a sensor that is implanted within a vessel, the central location within the vessel places the sensor in an optimal position for gathering data within the blood flow stream.

In addition, because the fixation member is comprised of a flexible, compressible material, the implantable medical device may be inserted into the body while in compressed form. In the compressed form, the fixation member occupies less space, and as such the procedure for insertion is less invasive. For example, the implantable medical device with the fixation member in a compressed form may be inserted through a standard catheterization procedure. A physician can implant medical device by making an incision in the skin, introducing an insertion device such as a catheter into the body of the patient, guiding the insertion device to a target site, pushing medical device out of the insertion device, and withdrawing the insertion device. For example, in some embodiments, the physician may implant a sensor in the pulmonary artery by placement though a catheter inserted into the femoral vein. The physician may access the femoral vein by making an incision in the inguinal region and then may feed the catheter through the femoral vein and inferior vena cava into the heart. The catheter may then be passed through the chambers of the right heart into the pulmonary artery, where the device may be deployed from the catheter into the pulmonary artery. The use of a small, collapsed device makes such a minimally invasive procedure possible. Once in place, the fixation member expands to a noncompressed, expanded form which secures the device in the desired position.

In general, implantation of a medical device in a compressed configuration is less invasive than an open surgical procedure to implant the medical device in its expanded configuration. The medical device can be delivered to a target site in a miniature configuration, and expand on its own to its enlarged configuration such as by absorbing fluid from the local environment, such as from the blood or interstitial fluid. In some cases, a fluid can be injected into the implantation site to accelerate expansion. Once in position, the fixation member is allowed to expand to hold the implantable medical device in the chosen location.

The ability of the fixation member to maintain either a compressed form or an expanded form is provided by the nature of the material used for the fixation member. In some embodiments, the fixation member is comprised of a hydrogel. Prior to implantation, the hydrogel fixation member is dry or dehydrated. Once in position, fluid such as water present in the patient's blood or tissues or supplied to the site by the physician is absorbed by the hydrogel, causing it to swell and assume a decompressed or expanded form which then holds the implantable medical device in position.

Embodiments of the invention include an operative component such as a sensor surrounded by a housing, and a fixation member affixed to and surrounding the housing. The fixation member is an annular structure including an ring shaped annulus and at least one resiliently deformable strut connecting the housing to the annulus. The strut includes a proximal end portion attached to the housing and a distal end portion attached to the annulus. In some embodiments, the strut may be curved in a manner that predisposes the strut to bow circumferentially rather than axially or longitudinally when placed under compressive load.

The medical device is configured to be implanted in a human or animal body. In some embodiments, the medical device includes a microstimulator or a sensor as the operative component. When the operative component is a microstimulator, it may be a neurostimulator or muscle stimulator, for example. When the operative component is a sensor, the sensor may be configured to sense one or more conditions including, for example, blood pressure, blood flow, temperature, tissue hypotonicity, contractile force, pH, oxygen, carbon dioxide, chemical concentration, electrical parameters, or the like. The operative component of the medical device may be self-contained in that it is not physically coupled to any other medical device by a lead or other connection. For example, the operative component may receive power from, and/or wirelessly communicate with, an external control device. In another embodiment, the operative component may operate with an internal power supply. The invention is not limited to any particular operative component or any particular location of implantation. Nor is the invention limited to self-contained operative components, but encompasses operative components that include leads or that are otherwise not self-contained.

Figure 2:
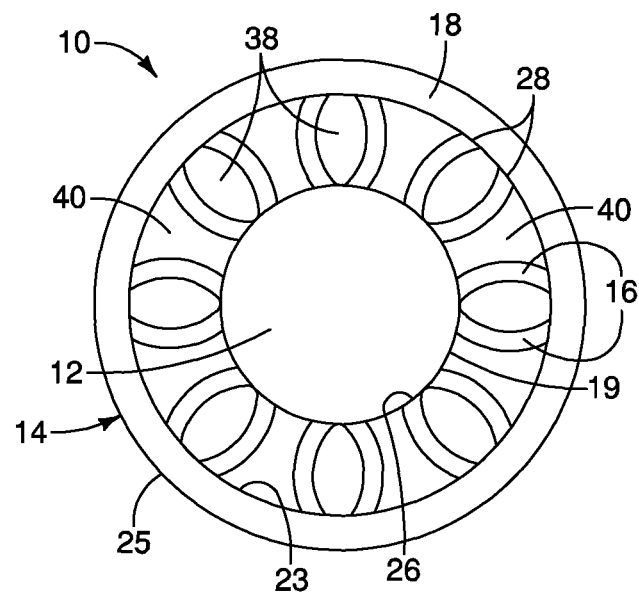
FIG. 2 is a perspective view of the device of FIG. 1 in an expanded state.

One embodiment of a medical device is shown in FIGS. 1 and 2. In FIG. 1, the medical device 10 is shown with the fixation member 14 in a compressed, unexpanded form, while in FIG. 2 the fixation member 14 has expanded. As can be seen, in the unexpanded form, the medical device 10 has a smaller diameter (transverse to the longitudinal axis) and occupies less volume, allowing for easier placement. The medical device 10 is therefore in this form prior to implantation and during insertion into the body. The medical device 10 may be sized to fit within a bore of an insertion device such as needle, hollow trocar, endoscope, catheter or cannula. In some embodiments, the device 10 in unexpanded form may be sized to fit through a catheter when oriented substantially parallel to the axis of the catheter. The dimension of the medical device 10 in the compressed or non-expanded form may be comparable to that of the housing 12 itself. In some embodiments, the device 10 in the compressed or dehydrated state can be approximately one to seven millimeters in diameter (transverse to its longitudinal axis) and approximately ten to twenty millimeters in length (parallel to its longitudinal axis). The invention encompasses other shapes and dimensions as well. The dimensions of medical device 10 can depend upon the internal components of housing 12.

In the expanded form shown in FIG. 2, the medical device 10 is able to engage the lumen or other location into which it has been placed. It assumes this form after placement at the desired location by absorbing fluid from the environment, such as from the blood. In the expanded state, the diameter of the device 10 may be approximately at least two times that of the device 10 in the compressed state. In some embodiments, the diameter may be at least approximately three times that of the device 10 in the compressed state. The degree of expansion can be regulated by the composition of the material of the fixation member. For example, a hydrogel can be configured to expand approximately two to five times when hydrating.

In embodiments in which the expandable fixation member 14 is comprised of a hydrogel, the compressed form may be described as dehydrated and the expanded form may be described as hydrated. However, the terms dehydrated and hydrated describe relative states rather than absolute conditions. For example, dehydrated does not necessarily mean that the fixation member 14 is completely devoid of fluid, but rather that it is more devoid of fluid than in the hydrated state. From the perspective of the hydrated state, hydrated does not necessarily mean that the polymeric matrix is saturated with fluid, but rather that it includes more fluid than in the dehydrated state.

The implantable device 10 includes a housing 12 containing the operative component and a fixation member 14 affixed to or integral with the housing 12. The fixation member 14 is deformable and, in this embodiment, includes a plurality of struts 16 and an annular member or annulus 18.

The housing 12 may be comprised of a biocompatible and thrombosis-inhibiting material which forms a hermitic seal. For example, the housing 12 may be made from, or the outer surface of the housing 12 may be coated with, a biocompatible material such as polyurethane, silicone, titanium, stainless steel, fluoropolymer or hydrogel. The components contained within the housing 12 will depend upon the function of the operative component. In some embodiments, such as embodiments in which the operative component functions as a sensor, the operative component may include a sensor, such sensor may be an accelerometer to measure sounds such as heart valve closures or heart muscle movements or a sensor, such as a sensor configured to sense conditions such as pressure, flow, temperature, hypotonicity or tissue fluid level, contractile force, pH or chemical concentration, a high performance battery as a power supply, a signal detection unit, a signal processing unit, a buffer memory, a transceiver unit, an associated antenna, and a controller for controlling the functions of the device 10. When the operative component is a self-contained stimulator, for example, it may contain components such as a pulse generator, a wireless telemetry interface, a power supply and a processor that controls delivery of stimulations. The housing 12 could combine both sensor capability and stimulator with telemetry in one package as an alternative embodiment.

The housing 12 may be of any suitable shape and configuration. In the embodiment shown, the housing 12 as viewed in plan has a circular periphery or outer surface 19, though other shapes are also possible. It has an anterior end 20 which is oriented upstream when placed inside a vessel and a posterior end 22 which is oriented downstream when placed inside a vessel. In this embodiment the anterior end 20 and the posterior end 22 are convex, but these configurations are purely illustrative and one or either could be planar.

The fixation member 14 includes an annulus 18 which is generally circular or ring shaped and circumscribes the housing 12. The annulus 18 has a circular inner surface 23 defining a central lumen and a circular outer surface 25. The outer surface 25 of the annulus 18 forms the outer periphery of the implantable device 10 and is the surface which engages the surrounding tissue such as the vessel wall. The annulus 18 is resiliently deformable and is in the form of a thin layer, having a relatively short radial dimension between the inner surface 23 and the outer surface 25 so as to minimize the obstruction to blood flow after implantation.

The fixation member further includes struts 16 which interconnect the housing 12 with the annulus 18. Each of the struts 16 is elongated and has an inner proximal end 26 and an outer distal end 28. Like the annulus 18, the struts are comprised of a resilient and expandable material. The struts 16 are capable of being folded or rolled very compactly when the implantable device is to be inserted into the vessel cavity, as shown in FIG. 1. The proximal end 26 of each strut is attached to the housing 12 and the distal end is attached to the inner surface 23 of the annulus 18. In the embodiment shown, each of the struts 16 has the same shape and length from proximal end 26 to distal end 28. Because of the uniform length of the struts 16, the housing 12 is centered by the struts 16 in the central axis of the annulus 18. The struts 16 and the annulus 18 may be made of the same material or each may be made of a different material. In some embodiments, the struts 16 and the annulus 18 are integrally molded of a hydrogel which expands to become pliable and resilient in its hydrated state.

The struts 16 extend radially outward from the housing 12 forming an array of struts 16 which are spaced apart to form a plurality of spaces. These spaces, while not unacceptably weakening the fixation member 14, provide several advantageous functions. For example, the spaces also allow for free passage of fluids around the housing 12 and through the fixation member 14. In addition, the presence of spaces within the fixation member 14 makes the fixation member 14 less bulky, which in turn makes it more amenable to being tightly rolled or folded when configured in its dehydrated state. This allows the device 10 to be readied in a reduced overall diameter dimension state for insertion into the vessel or cavity.

In some embodiments, the struts 16 extend extends from the outer surface 19 of the housing 12 in a radial plane which is generally perpendicular to the longitudinal axis of the device (extending through the center of the device from the anterior end 20 to the posterior end 22 of the housing 12). In other embodiments, the struts 16 are not perpendicular to longitudinal axis of the device but rather are angled toward either the anterior end 20 or the posterior end 22 of the housing 12. In such embodiments, the struts 16 do not lie within a single plane but rather may be imagined to form a discontinuous cone surrounding the housing 12, with each strut 16 at the same angle relative to the longitudinal axis of the device 10. For example, the struts 16 may be at an angle of about 20 to about 90 degrees relative to the longitudinal axis of the device. In some embodiments, the struts are at an angle of about 45 to about 75 degrees relative to the longitudinal axis of the device. In the embodiment shown in FIG. 3, a strut 16 is shown which extends radially outward from the housing 12 and anteriorly, toward the anterior end 20 of the housing 12. In such an embodiment, the housing 12 is urged posteriorly after implantation as the hydration of the hydrogel fixation member occurs within the body using fluid at the site in which the device is implanted.

Figure 3:
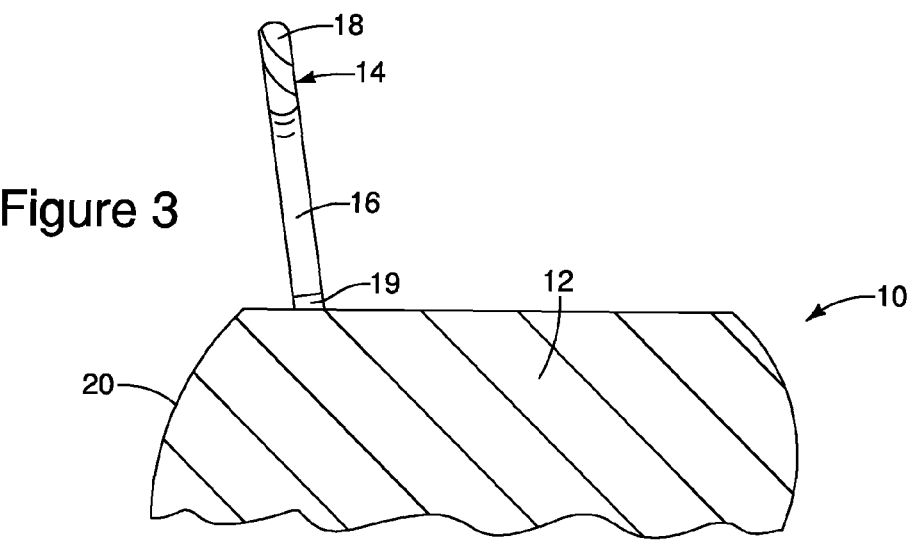
FIG. 3 is a partial side view of a device in an expanded state.

The struts 16 may attach to the housing 12 at a location at or near the anterior end 20 of the housing 12 as shown in the embodiment in FIG. 3. Alternatively, the struts 16 may attach to the housing 12 at or near the center of the housing 12, approximately midway between the anterior and posterior ends 20, 22, or may attach to the housing 12 at or near the posterior end 22 of the housing 12. In some embodiments, the device 10 may include only a single fixation member 14 which may be located proximally, centrally or distally on the housing 12. In other embodiments, the device 10 may include a plurality of fixation members 14. For example, in some embodiments, the device 10 may include only two fixation members. One fixation member 14 may be located at or near the anterior end 20 and the other may be located at or near the posterior end 22 of the housing 12. Alternatively, one fixation member may be centrally located on the housing, while the other may be at the anterior end 20 or the posterior end 22. Each of the plurality of fixation members 14 may be the same size (that is, they may have the same diameter when expanded) or one or the other may be larger or smaller as desired to fit securely within the desired location of implantation.

Figure 4:
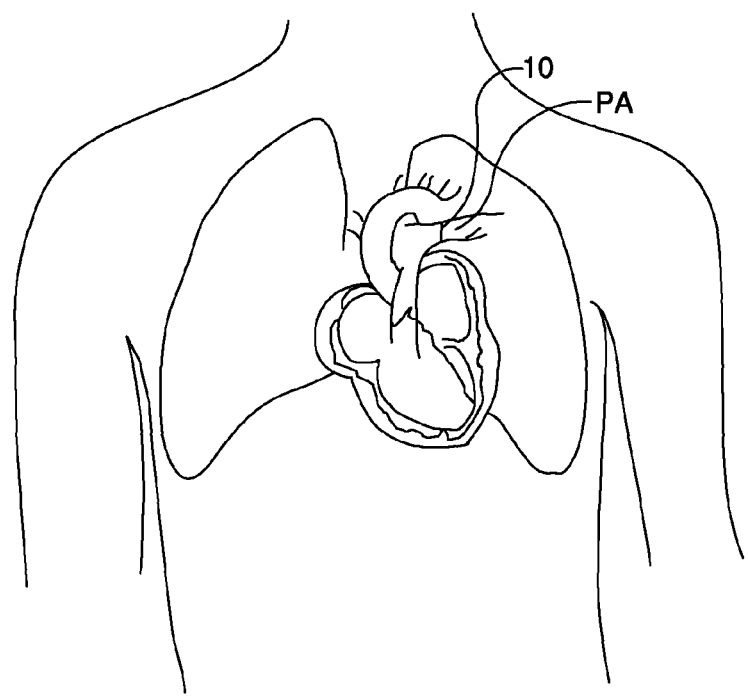
FIG. 4 is a diagram of a human chest including the heart and pulmonary arteries and an implanted medical device.
Figure 5:
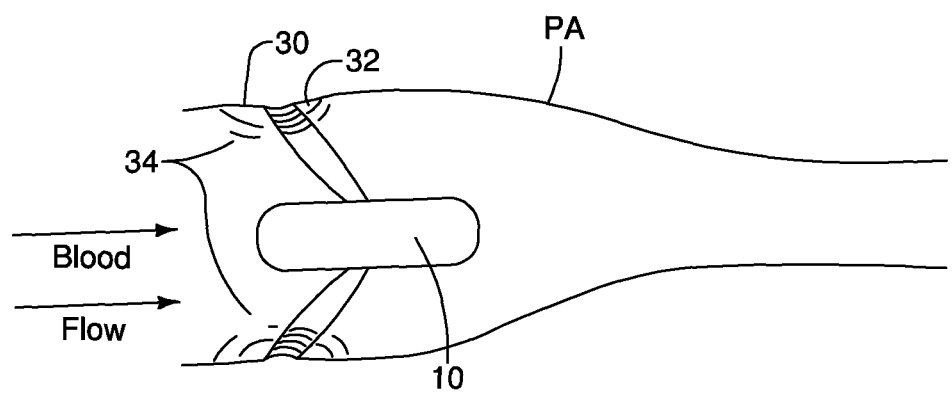
FIG. 5 is a side view of a device within a vessel.

After the device 10 is implanted into a lumen, such as the lumen of a vessel, the outer surface 25 of the annulus 18 is positioned to be pressed against the inner surface of the lumen. In response to this physical contact, over time, encapsulation tissue including fibroblasts and fibrous tissue may extend and grow around the annulus 18. An example of such tissue encapsulation is shown in FIGS. 4 and 5. In FIG. 4, the device 10 can be seen after implantation in the pulmonary artery. In FIG. 5, encapsulation tissue 32 can be seen growing from the vessel wall 30 around the annulus 18. The growth of this encapsulation tissue 32 can be beneficial for anchoring the device in position. However, it can also cause the diameter of the vessel to become smaller at this location, as shown by radial shrinkage at 34. This shrinkage exerts a generally radial compressive force on the annulus 18, which is transmitted to the housing 12 along the struts 16. Without compensating for these forces, the resilient struts 16 may deform by angling anteriorly or posteriorly and thereby moving the housing 12 more anteriorly or posterior within the vessel. For example, in embodiments such as that shown in FIG. 3, where the struts 16 are angled slightly anteriorly, this compressive force could cause the struts 16 to angle even further anteriorly over time, thereby moving the housing 12 further posteriorly. This posterior movement of the housing 12 may or may not be desirable depending on the location of the implanted medical device 10 and what other tissue or structure is in close proximity of the device housing 12. Therefore, in some embodiments, the fixation member 14 is designed to flex circumferentially, that is, in a circular manner around the longitudinal axis, to absorb some or all of the radial compressive force caused by tissue encapsulation.

In some embodiments, the struts 16 may be straight, extending directly from the housing 12 to the annulus 18 by the shortest path possible. However, in other embodiments, the struts 16 may be curved in a manner which predisposes the struts to compressing or deforming in a generally circumferential direction rather than in an axial or longitudinal direction when placed under a compressive load of the type that maybe applied by the wall of the vessel or cavity in which the device 10 is implanted. By configuring the fixation member 14 to resiliently flex or deform in a generally circumferential direction, tipping of the housing 12 to these forces is reduced or may be virtually eliminated, and normal sensing by the device may be maintained.

The embodiment shown in FIGS. 1 and 2 demonstrates one manner in which the fixation member 14 can be designed to compress radially and circumferentially rather than buckling or compressing anteriorly or posteriorly. In this embodiment, the struts 16 are arranged in pairs in a spoke-like fashion around the housing 12. The proximal ends 26 of each of the two struts 16 in the pair are closely spaced at their attachment points to the housing 12. Similarly, the distal ends 28 of the two struts 16 of the pair are closely spaced at their points of attachment in the annulus 18. Between the proximal ends 26 and the distal ends 28, the two struts 16 of each pair are curved away from each other. As such, the struts 16 or each pair curve symmetrically in opposite circumferential directions with respect with each other, such that they form a concave surface facing each other. The struts 16 are curved in a circumferential direction even when in an unloaded condition, prior to being placed under the compressive stress of the encapsulating tissue shrinkage. Between the two struts 16 of each pair are radially elongated openings 38 which are convex and which extend radially between the housing 12 and the annulus 18. The adjacent strut 16 pairings are spaced circumferentially to provide openings 40 which are generally concave in shape. As such, convex openings 38 and concave openings 40 are arrayed around the housing 12 in alternating fashion. The curved shape of the struts 16, which is present even in an unloaded state, predisposes the struts 16 to curving or bowing further in the same direction as their curvature when placed under a load, rather than buckling or compressing in an axial/ longitudinal direction. As such, when a compressive force is applied to the fixation member 14, it is predisposed to flexing in a circumferential direction with the struts 16 curving further to form a greater curve than when unloaded, increasing the space between the struts 16 of each facing pair and therefore the width of the convex spaces 38 and decreasing the space between adjacent strut 16 pairs and therefore the width of concave openings 40.

Figure 6:
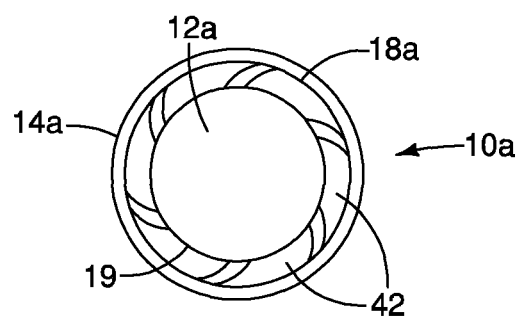
FIG. 6 is a perspective view of an alternative embodiment of a device in an unexpanded state.
Figure 7:
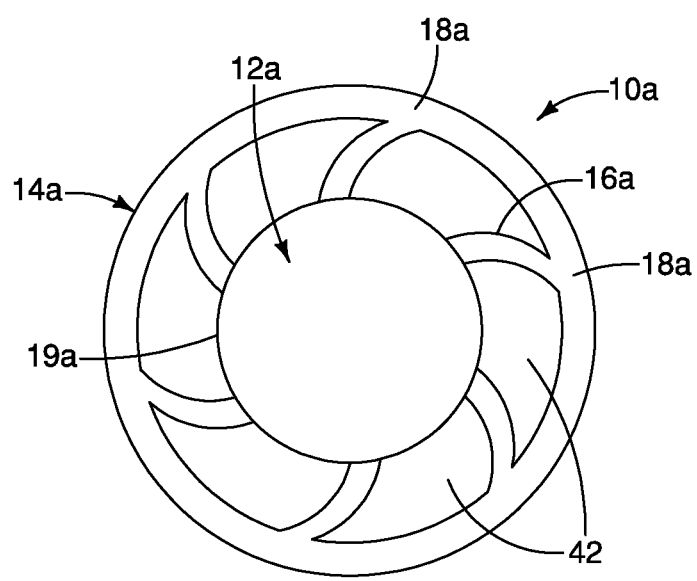
FIG. 7 is a perspective view of the device of FIG. 6 in an expanded state.

A second embodiment is shown in FIGS. 6 and 7. Each of the elements in these figures corresponding to equivalent elements in FIGS. 1 and 2 is designated by the same reference numeral, followed by the letter "a". Thus in this figure, device 10a is comprised of a housing 12a and a fixation member 14a for supporting the housing 12a. The fixation member 14a is further comprised of an annulus 18a and a plurality of struts 16a, which interconnect the housing 12a with the annulus 18a. The struts 16a are generally arranged in a spoke-like fashion around the housing 12a, but in this embodiment the struts 16a and are spaced uniformly. Alternatively, the struts 16a could be spaced in a circumferentially non-uniform manner. In this embodiment, each strut 16a is curved in the same circumferential direction, even when in an uncompressed state. This curving of the struts 16a predisposes the struts 16a to bow or curve even father in that same circumferential direction when compressively loaded in a generally radial direction. Elongated openings 42 lie between adjacent struts 16a and extend radially and somewhat circumferentially between the housing 12a and the annulus 18a. This embodiment provides the same advantages as those provided by the previous embodiment, including substantial elimination of an undesirable tipping or anterior or posterior movement of the housing 12a due to axial deformation of the struts 16a under compressive forces. Rather, when a compressive force is applied, the increased curving of the struts 16a brings the annulus 18a closer to the housing 12a, shortening the radial length of openings 42. In alternative embodiments, the struts 16a may be straight or linear rather than curved and may be positioned at an angle of less than 90 degrees relative to the housing 12a and the annulus 18a. For example, the struts 16a may be connected to the housing 12a at an angle of about 30 to about 90 degrees relative to the housing 12a as measured transverse to the longitudinal axis, such as about 30 to about 85 degrees, or about 45 to about 80 degrees. By being angled in this way, when the device 10a is placed under a compressive pressure, the struts 16a would be predisposed to bend in the direction in which they are angled, either by curving or by forming a more acute or smaller angle relative to the housing 12a.

The material which is used for forming the fixation member 14, 14a must be compressible and expandable as well as resilient. Examples of such material include silicone and hydrogel. The hydrogel may be a pure hydrogel, or a blend of hydrogel and one or more other materials, such as a blend of silicone rubber and hydrogel, polyacrylonitrile copolymers or a polymeric matrix including an osmotic agent. The use of a hydrogel in the desiccated state provides the advantage of swelling in an aqueous environment such that it can increase in size to its expanded shape after deployment at the desired location of implantation by absorbing liquid from the local environment, as well as being a resilient and flexible material.

Hydrogels useful in embodiments of the invention include polymers such as crosslinked polymers of water soluble or hydrophilic monomers and copolymers of water soluble and water insoluble monomers. For example, the hydrogel may include homopolymers and copolymers of acrylamides, methacrylamide, acrylate and methacrylate esters having at least one hydroxyl group on the side chain, such as 2-hydroxyethyl methacrylate, hydroxyethoxyethyl methacrylate, hydroxydiethoxy methacrylate, 2,3 dihydroxypropyl methacrylate, and glycerol methacrylate. Other suitable hydrogel forming polymers include polymers and copolymers of monomers such as methoxyethylethoxyethyl methacrylate, methoxydiethoxyethyl methacrylate, methoxyethyl methacrylate, methacrylate acid, vinyl alcohol, vinyl acetate, N-vinyl-2-pyrrolidone and related N-alkenyl-2-pyrrolidones, N-vinyl carbazole, N-vinyl succinimide, N-(−3-picolyl) methacrylamide, N-vinylimidazole, and vinylpyridine. In some embodiments, the hydrogel forming polymer is poly(N-vinyl pyrrolidone) polymerized with 2.0 wt % to 2.5 wt % tetraethyleneglycoldiacrylate. Other hydrogel forming polymers which may be used include poly-2,3-dihyhdroxypropyl methacrylate, copolymers of N-vinyl pyrrolidone and 2-hydroxyethyl methacrylate, copolymers of N-vinyl pyrrolidone and N-vinylcarbazole, copolymers of N-vinyl succinimide, copolymers of N-vinylpyrrolidone and N-(−3-picolyl)methacrylamide, and copolymers of N-vinyl pyrrolidone and 4-vinylpyridine. Other hydrogel materials may be useful include the polyacrylonitrile copolymers as described in U.S. Pat. Nos. 4,943,618 and 5,252,692, which are incorporated herein by reference. Cross-linked hydrogels may also be useful in embodiments of the present invention.

In general, hydrogels can assume a dehydrated state and a hydrated state. A hydrogel element in its dehydrated state is generally substantially smaller than the element in its hydrated state. A hydrogel element in its dehydrated state, when implanted in the body of a patient and placed in contact with body fluids, absorbs water and expands, assuming a hydrated state. For example, the hydrogel may absorb fluid from blood in the vessels, interstitial fluid in the tissues, or water or other fluid supplied to the device at the implantation site.

By controlling relative amounts of copolymers, it is often possible to regulate physical qualities of the hydrogel such as flexibility and amount of expansion. The particular type of hydrogel (e.g., amount of cross-linking between the polymer chains forming the hydrogel) or quantity of pure hydrogel in the mixture is selected to provide a desired amount of expansion of fixation member 14, 14a. The composition of the hydrogel may be further selected to provide for expansion of the fixation member 14, 14a within a certain time range, such as within one to ten minutes after exposure to body fluids or other fluids. The rate of deployment may be further controlled by applying an outer coating of a soluble material, such as mannitol, around the compressed fixation member 14, 14a, such that the coating dissolves before the hydrogel begins to hydrate.

The fixation member 14, 14a made from hydrogel may be formed to extend from the housing 12, 12a by any suitable method of forming hydrogel structures. For example, the hydrogel members may be initially formed in a first shape. While hydrogel fixation member 14, 14a is in an expanded state, the first shape may be cut, molded or otherwise shaped to form the struts a 16, 16 having the desired curves and the annulus 18, 18a. Hydrogel fixation members 14, 14a may be subsequently desiccated to the unexpanded, dehydrated state prior to implantation in a patient.

One method for forming the assembly of the implantable device 10, 10a utilizes a properly configured mold having the appropriate dimensioned cavities to form the fixation member 14, 14a struts 16, 16a and annulus 18, 18a. For example, the fixation member 14, 14a may be formed by positioning housing 12, 12a within the mold and introducing the hydrogel polymer formulation into the mold. The housing 12, 12a could, in an alternative embodiment, have a circumferential groove (not shown) which is filled with the hydrogel formulation and thus provides further engagement of the housing to the fixation member 14, 14a. Alternatively, the method for constructing the hydrogel fixation member 14, 14a may be by computer controlled milling of the prescribed shape from xerogel (a fully dehydrated hydrogel sheet of pellet form). The dimensions for the fixation member 14, 14a may be initially prepared with the subsequent reconfiguration dimension of the assembled fixation member to its targeted rehydrated dimension in mind. For example, one would prepare the xerogel which would have both dimension and tensile properties that after rehydration would meet the targeted final design. Adherence of the fixation member 14, 14a to the housing 12, 12a would be achieved by a compression engagement at the point of contact between the fixation member 14, 14a and the housing 12, 12a. Optionally, a biocompatible adhesive could adhere the fixation member 14, 14a to the housing 12, 12a.

During implantation, fixation member 14, 14a may be prevented from expanding by preventing it from being exposed to fluids. For example, during implantation, hydrogel fixation members 14, 14a may be separated from fluids until the device 10, 10a is located proximate to the implantation site by separating the fixation member 14, 14a from surrounding tissue by using an introducer, such as a catheter, a delivery sheath, trocar or needle, and/or a substantially water impermeable, biodegradable coating. Upon deployment from the introducer, the fixation member 14, 14a contacts blood and/or surrounding tissue which carry fluid (e.g., water in the blood, interstitial fluid), and the fixation member 14, 14a expands. This allows the device 10, 10a to maintain a relatively small profile (e.g., overall diameter) during implantation despite having a larger fixation member 14, 14a after expansion.

The medical device 10, 10a may be used with a programmer, which may be a handheld computing device that permits a clinician to control and monitor the device 10, 10a and download data from the device 10, 10a and may support telemetry (e.g., radio frequency (RF) telemetry) to allow a clinician or other individual to communicate with the device 10, 10a. The device 10, 10a may include a signal generator coupled to power source. The power source may be a small, rechargeable or non-rechargeable battery, or an inductive power interface that transcutaneously receives inductively coupled energy. In the case of a rechargeable battery, power source similarly may include an inductive power interface for transcutaneous transfer of recharge power. The device 10, 10a may include a process or such as a microprocessor, a controller, a DSP, an ASIC, an FPGA, discrete logic circuitry, or the like. The device 10, 10a may further include memory, such as any volatile or non-volatile media, such as a RAM, ROM, NVRAM, EEPROM, flash memory, and the like, which may record and store sensed physiological data, for example.

Although the invention is described as useful in applications with cardiac monitoring, the invention is not limited to that application. Furthermore, the invention can be deployed via implantation techniques in addition to those described above. The invention further includes within its scope methods of making and using the implants described above.

Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. An implantable medical device comprising:
   an operative component and a housing surrounding the operative component;
   a resiliently deformable fixation member for supporting the housing, the fixation member comprising:
   a ring shaped annulus circumscribing the housing;
   a plurality of elongated struts having a proximal end affixed to the housing and a distal end affixed to the annulus; and
   wherein the resiliently deformable fixation member is comprised of a hydrogel; and
   wherein the struts are curved in shape between the proximal and distal ends; and
   wherein the struts are spaced in pairs with each strut curving away from the other of its pair between their proximal and distal ends in a circumferential direction.

2. An implantable medical device comprising:
   an operative component and a housing surrounding the operative component;
   a resiliently deformable fixation member for supporting the housing, the fixation member comprising:
   a ring shaped annulus circumscribing the housing;
   a plurality of elongated struts having a proximal end affixed to the housing and a distal end affixed to the annulus; and
   wherein the resiliently deformable fixation member is comprised of a hydrogel; and
   wherein the struts are curved in shape between the proximal and distal ends; and
   wherein the struts are all curved in the same circumferential direction.

3. The implantable medical device of claim 2 wherein the struts are approximately evenly spaced around the housing.

* * * * *